(12) United States Patent
Greenberg et al.

(10) Patent No.: US 9,265,599 B2
(45) Date of Patent: Feb. 23, 2016

(54) RETENTION SYSTEM FOR AN ENDOLUMINAL DEVICE

(75) Inventors: Roy K. Greenberg, Bratenahl, OH (US); Karl J. West, Geneva, OH (US)

(73) Assignee: CLEVELAND CLINIC FOUNDATION, Cleveland, OH (US)

( * ) Notice: Subject to any disclaimer, the term of this patent is extended or adjusted under 35 U.S.C. 154(b) by 561 days.

(21) Appl. No.: 13/598,095

(22) Filed: Aug. 29, 2012

(65) Prior Publication Data

US 2013/0053945 A1 Feb. 28, 2013

Related U.S. Application Data

(60) Provisional application No. 61/529,618, filed on Aug. 31, 2011.

(51) Int. Cl.
| | |
|---|---|
| A61F 2/06 | (2013.01) |
| A61F 2/07 | (2013.01) |
| A61F 2/954 | (2013.01) |
| A61F 2/24 | (2006.01) |
| A61F 2/89 | (2013.01) |
| A61F 2/95 | (2013.01) |

(52) U.S. Cl.
CPC . *A61F 2/07* (2013.01); *A61F 2/954* (2013.01); *A61F 2/24* (2013.01); *A61F 2/89* (2013.01); *A61F 2002/061* (2013.01); *A61F 2002/075* (2013.01); *A61F 2002/9511* (2013.01); *A61F 2250/006* (2013.01)

(58) Field of Classification Search
CPC ......... A61F 2/2418; A61F 2/856; A61F 2/24; A61F 2/2427; A61F 2002/072; A61F 2002/077; A61F 2/07; A61F 2/954; A61F 2002/075; A61F 2/89; A61F 2250/006; A61F 2002/9511; A61F 2002/061
USPC .................................................. 623/1.11–1.35
See application file for complete search history.

(56) References Cited

U.S. PATENT DOCUMENTS

| | | | |
|---|---|---|---|
| 5,873,906 A | 2/1999 | Lau et al. | |
| 6,102,938 A * | 8/2000 | Evans et al. .................. | 623/1.35 |
| 6,261,305 B1 | 7/2001 | Marotta et al. | |
| 6,350,277 B1 | 2/2002 | Kocur | |
| 6,352,553 B1 | 3/2002 | van der Burg et al. | |

(Continued)

FOREIGN PATENT DOCUMENTS

| | | |
|---|---|---|
| EP | 2491892 | 8/2012 |
| WO | WO 2007/124053 | 11/2007 |

OTHER PUBLICATIONS

European Search Report, EP 12182232, search report completed Nov. 9, 2012.

*Primary Examiner* — Amy R Weisberg
(74) *Attorney, Agent, or Firm* — Brinks Gilson & Lione

(57) ABSTRACT

A delivery system for an endoluminal device including an introducer, the introducer having a distal end intended to remain outside a patient in use and a proximal end. A stent graft having a first and second end is retained upon the introducer, the stent graft defining a fenestration disposed through a wall of the stent graft between the first and second end. A valve arrangement is disposed within an interior lumen of the stent graft about the fenestration. A retention system including a trigger wire engages and retains the valve arrangement away from the fenestration. The fenestration is in fluid communication with the interior lumen of the stent graft.

15 Claims, 4 Drawing Sheets

(56) References Cited

U.S. PATENT DOCUMENTS

| | | |
|---|---|---|
| 6,716,238 B2 | 4/2004 | Elliott |
| 2001/0049534 A1* | 12/2001 | Lachat ............................ 606/108 |
| 2002/0169497 A1* | 11/2002 | Wholey et al. ................ 623/1.13 |
| 2003/0199967 A1* | 10/2003 | Hartley et al. ................ 623/1.13 |
| 2003/0204243 A1* | 10/2003 | Shiu .............................. 623/1.16 |
| 2005/0059923 A1* | 3/2005 | Gamboa ............................ 604/9 |
| 2005/0131517 A1* | 6/2005 | Hartley et al. ................ 623/1.13 |
| 2006/0106450 A1 | 5/2006 | Muvhar |
| 2006/0247761 A1* | 11/2006 | Greenberg et al. ........... 623/1.16 |
| 2007/0067019 A1 | 3/2007 | Miller et al. |
| 2007/0067023 A1 | 3/2007 | Kveen et al. |
| 2007/0078511 A1 | 4/2007 | Ehr et al. |
| 2007/0250154 A1* | 10/2007 | Greenberg et al. ........... 623/1.13 |
| 2008/0114446 A1* | 5/2008 | Hartley et al. ................ 623/1.13 |
| 2008/0147163 A1* | 6/2008 | Allen ............................ 623/1.14 |
| 2008/0281399 A1* | 11/2008 | Hartley et al. ................ 623/1.13 |
| 2009/0043377 A1* | 2/2009 | Greenberg et al. ........... 623/1.35 |
| 2011/0313512 A1* | 12/2011 | Hartley et al. ................ 623/1.35 |
| 2012/0158121 A1* | 6/2012 | Ivancev et al. ................ 623/1.13 |
| 2012/0221094 A1* | 8/2012 | Cunningham et al. ........ 623/1.12 |
| 2012/0290069 A1* | 11/2012 | Ivancev et al. ................ 623/1.13 |
| 2013/0046371 A1* | 2/2013 | Greenberg et al. ........... 623/1.11 |
| 2013/0053945 A1* | 2/2013 | Greenberg et al. ........... 623/1.12 |
| 2013/0172984 A1* | 7/2013 | Greenberg et al. ........... 623/1.24 |
| 2014/0148888 A1* | 5/2014 | Barrand .......................... 623/1.2 |
| 2014/0257464 A1* | 9/2014 | Roeder .......................... 623/1.35 |
| 2014/0277335 A1* | 9/2014 | Greenberg et al. ........... 623/1.11 |
| 2014/0277369 A1* | 9/2014 | Roeder et al. ................. 623/1.13 |
| 2014/0316513 A1* | 10/2014 | Tang ............................. 623/1.16 |
| 2014/0364936 A1* | 12/2014 | Hartley ......................... 623/1.35 |
| 2014/0371838 A1* | 12/2014 | Buddery et al. .............. 623/1.11 |
| 2015/0012080 A1* | 1/2015 | Barrand ......................... 623/1.13 |

\* cited by examiner

RETENTION SYSTEM FOR AN ENDOLUMINAL DEVICE

RELATED APPLICATIONS

The present application claims priority to U.S. Provisional Patent Application Ser. No. 61/529,618 filed Aug. 31, 2011, the entirety of which is hereby incorporated by reference.

TECHNICAL FIELD

The present invention relates to a method and means for introducing implantable devices. More particularly, the present invention relates to a method and means for delivery of fenestrated implantable devices.

BACKGROUND

This invention relates generally to an endoluminal prosthesis and particularly to a endoluminal prosthesis having a fenestration that is implantable within the human or animal body for the repair of damaged vessels, ducts or other physiological passageways and cavities, and systems and methods for facilitating deployment of such an endoluminal prosthesis.

The physiological passageways and cavities of human and animal bodies, for example, blood vessels and ducts, occasionally weaken or even rupture. One common surgical intervention for weakened, aneurysmal or ruptured passageways or ducts involves the use of an endoluminal prosthesis to provide some or all of the functionality of the original, healthy passageway or duct and/or to preserve any remaining vascular integrity by replacing a length of the existing passageway or duct wall that spans the site of failure or defect. Endoluminal prostheses may be of a unitary construction or may be comprised of multiple prosthetic modules.

A modular prosthesis allows a surgeon to accommodate a wide variation in vessel morphology while reducing the necessary inventory of differently sized prostheses. For example, aortas vary in length, diameter and angulation between the renal artery region and the region of the aortic bifurcation. Prosthetic modules that fit each of these variables can be assembled to form a prosthesis, obviating the need for a custom prosthesis or large inventories of prostheses that accommodate all possible combinations of these variables. A modular system may also accommodate deployment options by allowing the proper placement of one module before the implantation of an adjoining module.

Generally, when deploying an endovascular prosthesis into a body lumen, it is possible to obtain access to such a body lumen from each end of the lumen where necessary, thereby facilitating placement of a device in the lumen. There can be problems, however, if the aneurysm of the aorta extends down into one or other of the iliac arteries. Each of the common iliac arteries branches into the internal and external iliac arteries and it is necessary in such a situation that a blood flow path can be directed through an endovascular stent graft into each of these arteries. The internal iliac artery which extends from the common iliac artery below the aortic bifurcation is for all intents and purposes a blind vessel because there is no practical way of performing an endovascular minimally invasive procedure into that vessel other than by entry from the common iliac artery.

BRIEF SUMMARY

In one aspect, a retention system for an endoluminal device includes a trigger wire associated with a deployment device to engage and retain a valve arrangement away from a fenestration.

In one aspect, the trigger wire exits a lumen of the endoluminal device through a second aperture on the interior wall adjacent to the self-sealing fenestration. In another aspect, the trigger wire exits a lumen of the endoluminal device through a proximal end. In another example, the trigger wire is retained upon the interior wall of the endoluminal device opposite the fenestration. With the valve in an open position, the fenestration is in fluid communication with the lumen of the stent graft, which allows for the deployment of other endoluminal devices through the fenestration.

In another aspect, a delivery system for an endoluminal device includes an introducer, the introducer having a distal end intended to remain outside a patient in use and a proximal end. A stent graft having a first and second end is retained upon the introducer, the stent graft defining a fenestration disposed through a wall of the stent graft between the first and second end. A valve arrangement is disposed within an interior lumen of the stent graft about the fenestration. A retention system including a trigger wire engages and retains the valve arrangement away from the fenestration. The fenestration is in fluid communication with the interior lumen of the stent graft. In some aspects, at least one restraining loop remains with the stent graft after deployment.

DETAILED DESCRIPTION OF THE DRAWINGS AND THE PRESENTLY PREFERRED EMBODIMENTS

Unless defined otherwise, all technical and scientific terms used herein have the same meaning as commonly understood to one of ordinary skill in the art to which this invention belongs.

The term "prosthesis" means any device for insertion or implantation into or replacement for a body part or function of that body part. It may also mean a device that enhances or adds functionality to a physiological system. The term prosthesis may include, for example and without limitation, a stent, stent-graft, filter, valve, balloon, embolization coil, and the like.

The term "endoluminal" refers to or describes the internal or inside of a lumen, duct, and other passageways or cavities located in a human or other animal body. A lumen or a body passageway may be an existing lumen or a lumen created by surgical intervention. As used in this specification, the terms "lumen" or "body passageway," and "vessel" are intended to have a broad meaning and encompass any duct (e.g., natural or iatrogenic) or cavity within the human body and may include without limitation, blood vessels, respiratory ducts, gastrointestinal ducts, such as the biliary duct, intestines, the esophagus, the pericardial cavity, the thoracic cavity, and the like. Accordingly, the terms "endoluminal device" or "endoluminal prosthesis" describe devices that can be placed inside or moved through any such lumen or duct.

The term "graft" or "graft material" describes an object, device, or structure that is joined to or that is capable of being joined to or implanted in or against a body part to enhance, repair, or replace a portion or a function of that body part. A graft by itself or with the addition of other elements, such as structural components, may comprise an endoluminal prosthesis. The graft may be comprised of a single material, a blend of materials, a weave, a laminate, or a composite of two or more materials. The graft may also be constructed from a synthetic, for example and without limitation, a polymer. The graft may be formed from a single layer or multiple layers of material. In embodiments employing a plurality of layers of material, the layers may remain separate, or may be attached to each other through a secondary process such as sintering, curing, adhesives, sutures or the like.

The terms "patient," "subject," and "recipient" as used in this application may refer to any animal, particularly humans.

In this description, the term "proximal" refers to a location which in use is closest to the patient's heart, in the case of a vascular implant, and the term "distal" refers to a location furthest from the patient's heart.

Figure 1:
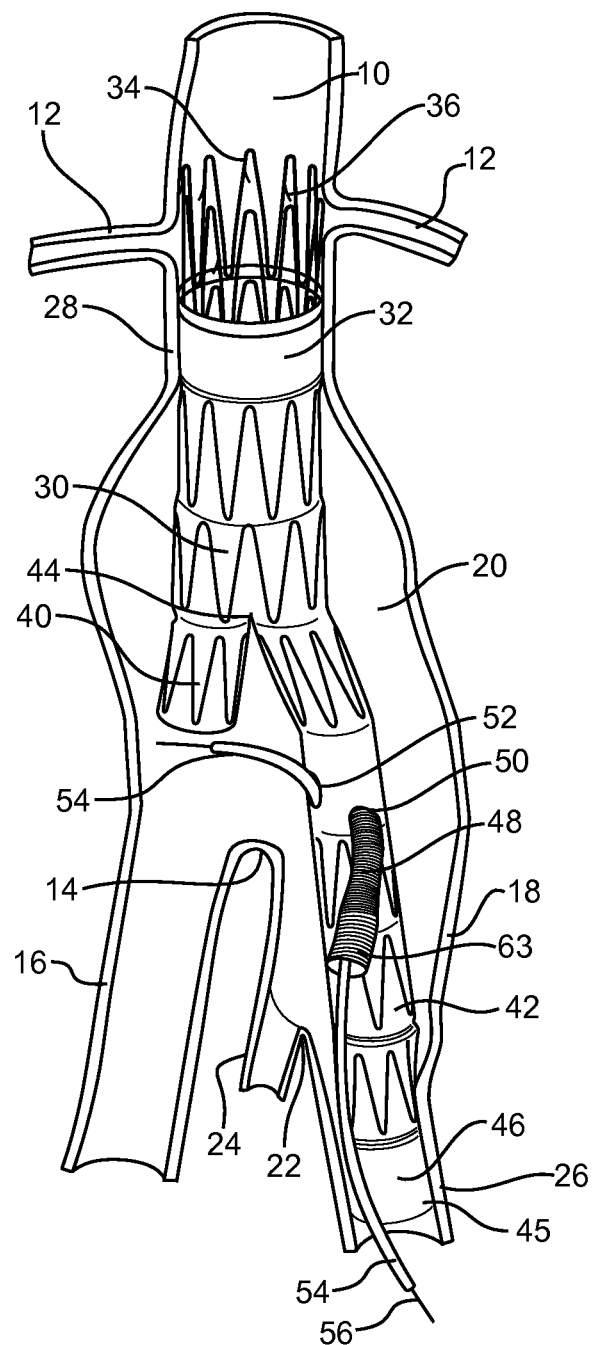
FIG. 1 is an embodiment of an endoluminal device having a self-sealing fenestration as it will be deployed into the vasculature before placement of an iliac side branch.

Looking more closely at the drawings, and in particular FIG. 1, it will be seen that a schematic view of part of the vascular arrangement of a patient is illustrated incorporating a stent graft. The vasculature comprises an aorta 10 in the region between the renal arteries 12 and the aortic bifurcation 14. Common iliac arteries 16 and 18 extend down from the aortic bifurcation 14. The aorta 10 has an aneurysm 20 which extends down into the common iliac artery 18 as far as the bifurcation 22 between the internal iliac artery 24 and the external iliac artery 26.

To traverse the aneurysm 20, an endoluminal device, such as a twin bifurcated aortic stent graft 30, has been deployed into the aorta 10. The stent graft 30 includes a proximal end 32, which is engaged into a non-aneurysed portion 28 of the aorta 10 just distal of the renal arteries 12. A proximally extending suprarenal stent 34 with barbs 36 is positioned on the proximal end 32 of the stent graft. The barbs 36 of the stent 34 engage the wall of the aorta 10 proximal of the renal arteries 12 to provide a secure position and to prevent the stent graft 30 from migrating following deployment into the aorta 10. The stent graft 30 also includes a short leg 40 and a longer leg 42 extending from the graft bifurcation 44. In this embodiment, the longer leg 42 has a sealing surface 46 at its distal end 45 which engages into a non-aneurysed portion of the external iliac artery 26.

The longer leg 42 includes a side arm 48 from its connection at a fenestration 50 into the longer leg 42. In this embodiment, the side arm 48 is in the form of a corrugated tube extending in a part helical manner from its connection at a fenestration 50 into the longer leg 42. The side arm 48 extends in a distal direction and helically partly around the longer leg 42 and has a distal end 63 remote from its connection with the longer leg 42 which opens adjacent to the internal iliac artery 24. A fenestration 52 is placed into the longer leg 42 proximal of the connection of the side arm 48 into the longer leg 42. During deployment of the stent graft into the vasculature of a patient an in-dwelling catheter 54 extends through the side arm 48 and out through the self-sealing fenestration 52. The in-dwelling catheter 54 includes a guide wire 56.

The stents of the stent graft 30 may be made from numerous metals and alloys. In one example, the stents comprise a shape-memory material such as a nickel-titanium alloy ("nitinol"). Moreover, the structure of the stents may be formed in a variety of ways to provide a suitable intraluminal support structure. For example, one or more stents may be made from a woven wire structure, a laser-cut cannula, individual interconnected rings, or another pattern or design. While one exemplary arrangement is shown in FIG. 1, it will be appreciated that the exact number of stents, and their location, may be varied.

In one example, shown in FIG. 1, the stents may be configured in the form of one or more "Z-stents," each of which may comprise a series of substantially straight segments interconnected by a series of bent segments. The bent segments may comprise acute bends or apices. The stents are arranged in a zigzag configuration in which the straight segments are set at angles relative to each other and are connected by the bent segments. However, the stents may comprise any suitable configuration and one or more stents may be provided.

The stent graft 30 may be constructed from a biocompatible material. Examples of biocompatible materials from which textile graft material can be formed include, without limitation, polyesters, such as polyethylene terephthalate; fluorinated polymers, such as polytetrafluoroethylene (PTFE) and fibers of expanded PTFE, and polyurethanes. For example, the stent graft 30 may be constructed from woven multifilament polyester, for example and without limitation, Dacron™, produced by DuPont. Dacron™ is known to be sufficiently biologically inert, non-biodegradable, and durable to permit safe insertion inside the human body.

Figure 2:
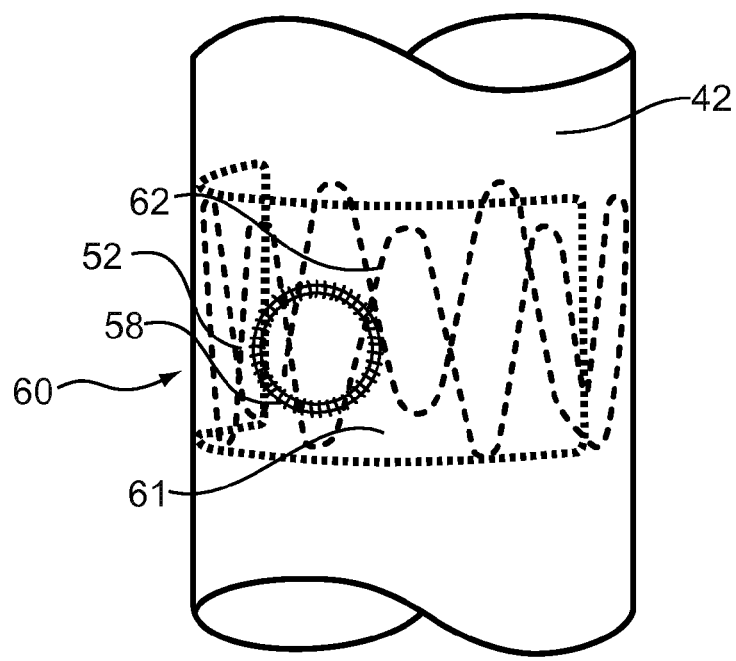
FIG. 2 is a schematic view of an embodiment of a stent graft having a self sealing fenestration.

FIG. 2 provides a more detailed view of a portion of the longer leg 42 of the stent graft 30. In this embodiment, the longer leg 42 of the stent graft 30 has a fenestration 52 defined by a peripheral resilient ring 58 which is stitched into the tube of the longer leg 42. The fenestration 52 has a valve arrangement 60 disposed about its surface. The valve arrangement 60 may include a semi-circular portion of biocompatible graft material 61 that is disposed within the lumen of the longer leg 42. A self-expanding stent 62 engages the valve arrangement 60 against the inside wall of the longer leg 42 and in particular over the fenestration 52. The expanding force of the stent 62 helps to close off flow therethrough the fenestration 52 from inside the longer leg 42 to outside.

Figure 3:
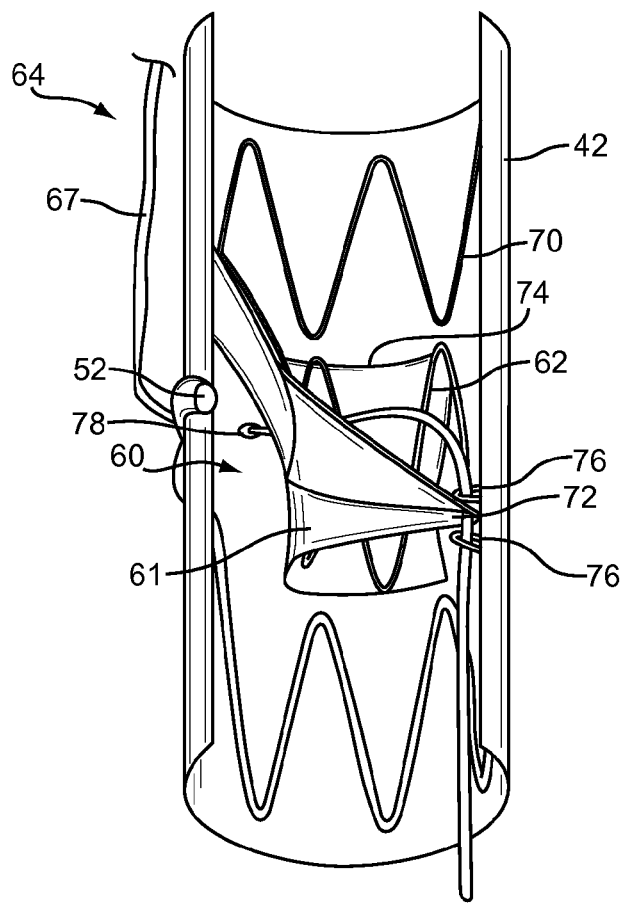
FIG. 3 is an embodiment of a retention system for deploying a valve of a self-sealing fenestration where the valve is in an open position.

FIG. 3 discloses an embodiment of a retention system 64 used in conjunction with a delivery device for deploying the longer leg 42 of a twin bifurcated stent graft. As shown, the longer leg 42 includes a plurality of self-expanding stents 70 about its outer surface. The longer leg 42 includes a fenestration 52 having a self-sealing valve arrangement 60. The valve arrangement 60 includes a sleeve of biocompatible graft material 61 and a self-expanding stent 62 configured to engage it against the interior wall of the longer leg 42 and in particular over the fenestration 52. The valve arrangement 60 is held in an open position by the retention system 64. In the open position, the fenestration 52 is in fluid communication with the lumen of the longer leg 42, which allows for the deployment of other endoluminal devices through the fenestration 52. Additionally, the valve arrangement 60 will not impede wires and/or devices entering the fenestration 52.

The retention system 64 includes a trigger wire 67. The trigger wire 67 captures the distal edge 72 of the valve arrangement 60 and pulls the valve arrangement 60 away from the fenestration 52 and near an interior wall of the longer leg 42. As shown, the trigger wire 67 is held in place by restraining loops 76 distal to the distal edge 72 of the valve arrangement 60 and proximal to the distal edge 72 of the valve arrangement 60. The restraining loops 76 may comprise a suitable biocompatible material, including, but not limited to, prolene. After passing through the distal edge 72 of the valve arrangement 60, the trigger wire 67 passes through an aperture located on the proximal end 74 of the valve arrangement 60. The trigger wire 67 exits the lumen 43 of longer leg 42 through an exit port 78 positioned adjacent the fenestration 52.

Figure 4:
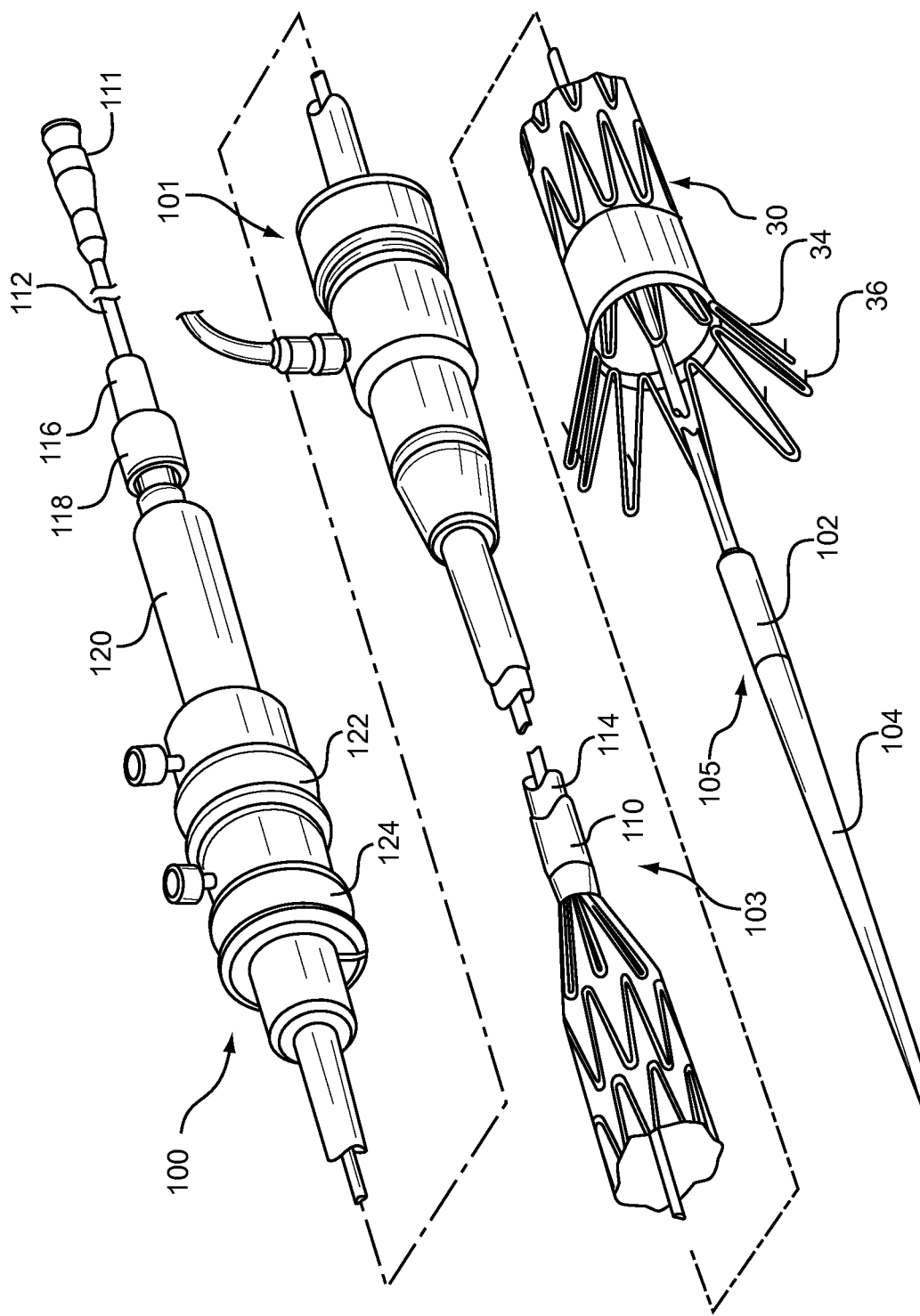
FIG. 4 shows an embodiment delivery device used with the retention system of FIG. 3 for deployment of an endoluminal device.

The retention system 64 may be used with various delivery systems for endoluminal devices, such as that described in U.S. Pat. No. 7,651,519, entitled "Prosthesis Deployment System," and U.S. Pat. No. 7,666,219, entitled "Prosthesis Deployment System Retention Device," both of which are incorporated herein by reference in their entirety. In the aspect shown in FIG. 4, the delivery system 100 for deploying a stent graft 30 in a lumen of a patient includes an external manipulation section 101, a distal positioning mechanism or attachment region 103, and a proximal positioning mechanism or attachment region 105. The external manipulation section 101, which is acted upon by a user to manipulate the introducer 100, remains outside of the patient throughout the procedure. The proximal attachment region includes a retention device 102. The retention device 102 has at its proximal end a long tapered flexible extension or dilator 104. A thin walled tube 112 generally made of metal is fastened to the extension 104. The thin walled tube 112 is flexible so that the introducer 100 can be advanced within a relatively tortuous vessel, such as the femoral artery. The thin walled tube 112 also allows manipulation longitudinally and rotationally of the proximal attachment region 105. The thin walled tube 112 extends throughout the introducer 100 to the manipulation section 101, terminating at a connection means 111. The connection means 111 is adapted to accept a syringe to facilitate the introduction of reagents into the thin walled tube 112. A tube 114 is coaxial with and radially outside the thin walled tube 112. The tube 114 is "thick walled," which is to say the thickness of the wall of tube 114 is several times that of the thin walled tube 112. A sheath 110 is coaxial with and radially outside the thick walled tube 112.

The external manipulation section 101 has a body 120 that is mounted onto the thick walled plastic tube 114, which passes through the body 120. When screwed in, vice jaws (not shown) clamp against and engage the thin walled tube 112, and the thin walled tube 112 can only move with the body 120, and hence can only move with the thick walled tube 114. A proximal wire release mechanism 122 and a distal wire release mechanism 124 are mounted for slideable movement on the body 120. A pin vice 118 is mounted onto the distal end of the body 120. The pin vice 118 has a screw cap 116. The positioning of the proximal and distal wire release mechanisms 122 and 124 is such that the proximal wire release mechanism 122 must be moved before the distal wire release mechanism 124 can be moved.

Figure 5:
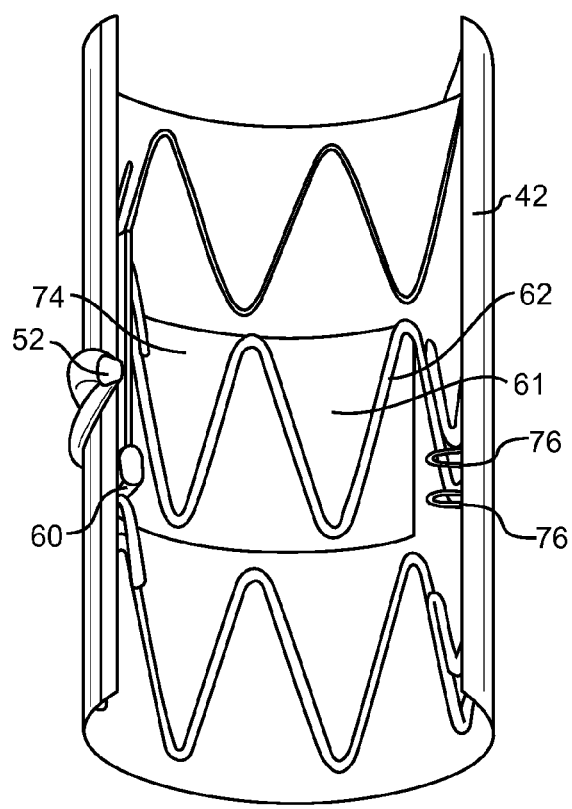
FIG. 5 shows the self-sealing fenestration of FIG. 3, where the valve is in the closed position.

FIG. 5 shows the longer leg 42 where the valve arrangement 60 of the fenestration 52 is in a closed position. After the stent graft 30 and any additional devices are deployed within diseased vessel of a patient, the trigger wire 67 of the retention system 64 is removed through the distal end 45 of the longer leg 42. In this aspect, the restraining loops 76 remain with the longer leg 42 after deployment. Upon removal of the trigger wire 67, the self-expanding stent 62 positioned on the internal surface of the valve arrangement 60 engages the inside wall of the longer leg 42, and thus, sealing the fenestration 52. The aperture on the proximal end 74 of the valve arrangement 60 and the exit port 78 are positioned on the valve arrangement 60 such that they are not in alignment. Accordingly, when the valve arrangement 60 is in the closed position, the aperture on the proximal end 74 of the valve arrangement 60 and the exit port 78 are also sealed by the valve arrangement 60.

In use, the operator deploys the introducer 100 over a guide wire and the introducer 100 into the patient through an artery, such as the femoral artery, via an incision and the introducer 100 is extended up into the aortic bifurcation, and positioned such that the dilator 104 is proximal of the renal arteries. The sheath 110 is withdrawn such that the stent graft 30 is exposed and the short leg 40 is deployed. Following deployment of the main body of the stent graft 30 and the short leg 40, the sheath 110 is further withdrawn into the iliac artery 18 to expose the longer leg 42 while retaining the distal end 45 of the longer leg 42. The trigger wire 67 of the retention arrangement 64 remains engaged with the distal edge 72 of the valve arrangement 60, leaving the valve arrangement 60 in the open position. The operator may introduce additional endoluminal prostheses, such as the in-dwelling catheter 54 for deploying a branch stent through the side arm 48 of the stent graft 30 into an internal artery, through the fenestration 52 while the valve arrangement 60 is in the open position. U.S. patent application Ser. No. 10/962,763 entitled "Introducer for Iliac Side Branch Device" discloses an arrangement for using an in-dwelling catheter to access an internal iliac artery and is herein incorporated by reference in its entirety.

Following deployment of the additional endoluminal prostheses through the fenestration 52, the operator may release and remove the trigger wire 67 of the retention system 64 in order to release the valve arrangement 60. Once the trigger wire 67 is removed from the distal edge 72 of the valve arrangement 60, the self-expanding stent 62 on the biocompatible graft material 61 engages the inner wall of the longer leg 42, and seals the fenestration 52, precluding access to the internal artery and prevents the possibility of leaks into the stent graft 30. The distal end 45 of the longer leg 42 is deployed by withdrawing the sheath 110, and the sealing surface 46 engages the walls of the iliac artery 18. The proximal end 32 of the stent graft 30 is released from the introducer 100, releasing suprarenal exposed stent 34 with barbs 36 engaging the wall of the aorta proximal of the renal arteries to provide a secure position to prevent migration of the stent graft 30.

Figure 6:
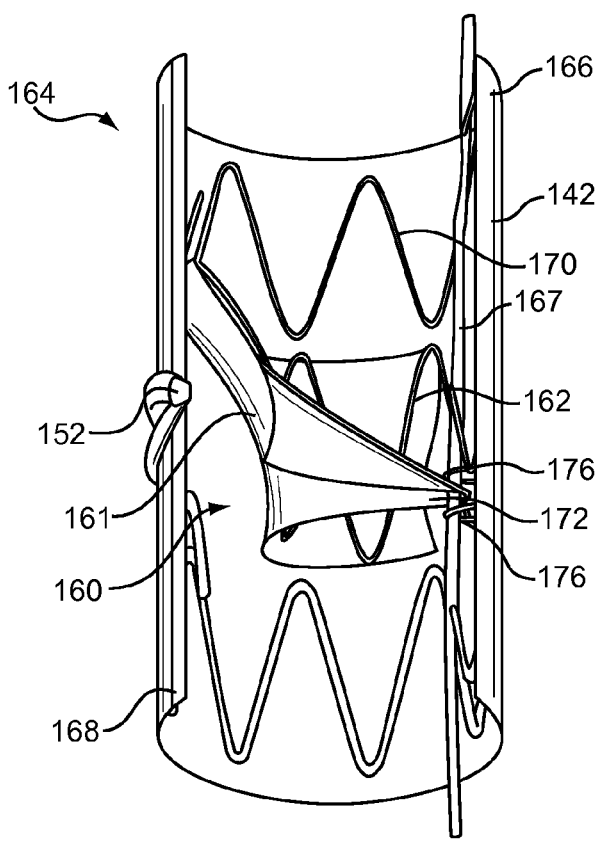
FIG. 6 is an alternative embodiment of a retention system for deploying a valve of a self-sealing fenestration where the valve is in an open position.

FIG. 6 shows an alternative embodiment of the retention system 164. As shown, the longer leg 142 includes a proximal end 166 and a distal end 168 and has a plurality of self-expanding stents 170 about its outer surface. The longer leg 142 includes a fenestration 152 having a self-sealing valve arrangement 160. The valve arrangement 160 includes a sleeve of biocompatible graft material 161 and self-expanding stent 162 configured to engage it against the interior wall of the longer leg 142 and, in particular, over the fenestration 152. The valve arrangement 160 of the longer leg 142 is held in an open position by a trigger wire 167 of the retention system 164. The trigger wire 167 captures the distal edge 172 of the valve arrangement 160 and pulls the valve arrangement 160 against the inside wall of the longer leg 142 opposite of the fenestration 152. The retention system 164 is held in position by restraining loops 176 distal to the distal edge 172 of the valve arrangement 160 and proximal to the distal edge 172 of the valve arrangement 160. After passing through the distal edge 172 of the valve arrangement 160, the trigger wire 167 exits the lumen of the longer leg 142 through the proximal end 166 of the leg 142. A self-expanding stent 162 is positioned on the internal surface of the valve arrangement 160 and is configured to engage it against the inside wall of the longer leg 142 and, in particular, over the fenestration 152.

Following the deployment of endoluminal devices through the valve arrangement 160, the trigger wire 167 of the retention system 164 is removed through the distal end 168 of the longer leg 142, and the valve released into a closed position. The removal of the trigger wire 167 allows the self-expanding stent 162 positioned on the internal surface of the valve arrangement 160 to engage the inside wall of the longer leg 142, and thus, seal the fenestration 152, and preclude access to an internal artery and prevent the possibility of leaks into the longer leg 142. In some aspects, at least one of the restraining loops 176 remains with the longer leg 142 after deployment.

Throughout this specification various indications have been given as to preferred and alternative embodiments of the invention. However, the foregoing detailed description is to be regarded as illustrative rather than limiting and the invention is not limited to any one of the provided embodiments. It should be understood that it is the appended claims, including all equivalents, that are intended to define the spirit and scope of this invention.

The invention claimed is:

1. A retention system for a delivery system comprising:
   an endoluminal device, comprising a trigger wire associated with a deployment device to engage and retain a valve arrangement of the endoluminal device away from a fenestration on the endoluminal device, where the trigger wire exits a lumen of the endoluminal device through a first aperture on an interior wall of the endoluminal device adjacent the fenestration, where the trigger wire engages a proximal portion of the valve arrangement through a second aperture on the valve arrangement.

2. The retention system of claim 1, where the valve arrangement comprises a sleeve of a biocompatible graft material and a self-expanding stent within the sleeve.

3. The retention system of claim 1, where the trigger wire is retained near the interior wall of the endoluminal device.

4. The retention system of claim 3, where the trigger wire is retained through the use of restraining loops.

5. The retention system of claim 4, where at least one of the restraining loops remains with a leg system after deployment.

6. The retention system of claim 3, where the trigger wire is retained upon the interior wall of the endoluminal device opposite the fenestration.

7. The retention system of claim 1, where the trigger wire engages a distal edge of the valve.

8. The retention system of claim 1, where the first aperture and the second aperture are not in alignment.

9. The retention system of claim 1, where the trigger wire extends from a handle of a delivery device of the endoluminal device and enters into the lumen of the endoluminal device distally.

10. A delivery system for an endoluminal device, comprising:
    an introducer, the introducer having a distal end intended to remain outside a patient in use and a proximal end;
    a stent graft having a first and second end retained upon the introducer, the stent graft defining a fenestration disposed through a wall of the stent graft between the first and second end;
    a valve arrangement disposed within an interior lumen of the stent graft about the fenestration; and
    a retention system comprising a trigger wire to engage and retain the valve arrangement away from the fenestration, where the fenestration is in fluid communication with the interior lumen of the stent graft, where the trigger wire exits the interior lumen of the stent graft through a first aperture on an interior wall of the stent graft adjacent the fenestration, and where the trigger wire engages a proximal portion of the valve arrangement through a second aperture on the valve arrangement.

11. The delivery system of claim 10, where the trigger wire engages a distal edge of the valve arrangement.

12. The delivery system of claim 10, where the trigger wire is retained upon the interior wall of the stent graft opposite the fenestration.

13. The delivery system of claim 12, where the trigger wire is retained through the use of restraining loops.

14. The delivery system of claim 13, where at least one of the restraining loops remains with the stent graft after deployment.

15. The delivery system of claim 10, where the trigger wire extends from a handle of a delivery device of the stent graft and enters into the lumen of the stent graft distally.

* * * * *